US00PP24642P2

(12) United States Plant Patent
van Zoest

(10) Patent No.: US PP24,642 P2
(45) Date of Patent: Jul. 15, 2014

(54) ***CLEMATIS* PLANT NAMED 'ZOCORO'**

(50) Latin Name: *Clematis*
Varietal Denomination: Zocoro

(75) Inventor: Jan van Zoest, Boskoop (NL)

(73) Assignee: J. Van Zoest Behler B.V., Boskoop (NL)

( * ) Notice: Subject to any disclaimer, the term of this patent is extended or adjusted under 35 U.S.C. 154(b) by 186 days.

(21) Appl. No.: 13/507,983

(22) Filed: Aug. 10, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

UPOV PLUTO Citations for 'Zocoro' May 2012.*

* cited by examiner

*Primary Examiner* — Wendy C Haas
(74) *Attorney, Agent, or Firm* — Penny J. Aguirre

(57) ABSTRACT

A new cultivar of hybrid *Clematis*, 'Zocoro', characterized by its nodding and double flowers, its flowers that are pale purple in color, its flowers that retain their color with very little fading, its sterility, and its cold hardiness to at least U.S.D.A. Zone 5.

3 Drawing Sheets

Variety denomination: 'Zocoro'

BACKGROUND OF THE INVENTION

The present invention relates to a new and distinct cultivar of *Clematis* of hybrid origin (Atragene Group) and will be referred to hereafter by its cultivar name 'Zocoro'. 'Zocoro' is grown as an herbaceous perennial for landscape use or as a flowering potted plant for the terrace.

'Zocoro' is derived from an ongoing breeding program by the Inventor at his nursery in Boskoop, The Netherlands. The goal of the selection was to select a hardy climber with uniquely colored and double flowers that could be grown for different purposes in the garden. 'Zocoro' was selected in 2007 and arose from a controlled cross made in 2004 between unnamed plants from the breeding program; the female parent designated as No. 20010039 (unpatented) and the male parent designated as No. 20040155 (unpatented).

Asexual reproduction of the new cultivar was first accomplished by internodial stem cuttings under the direction of the Inventor in Boskoop, The Netherlands in 2007. The characteristics of this cultivar have been determined to be stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zocoro' from other varieties of *Clematis* known to the Inventor.

1. 'Zocoro' exhibits nodding, double and wide opening flowers.
2. 'Zocoro' exhibits flowers that are pale purple (pink) in color with a slightly orange tint when flowers open in spring.
3. 'Zocoro' exhibits flowers that retain their color with very little fading.

4. 'Zocoro' is sterile, no seed is produced.
5. 'Zocoro' is cold hardy to at least in U.S.D.A. Zone 5.

'Zocoro' differs from its female parent in having pink flowers while the female parent has dark purple flowers. The male parent is lost and no records are available.

'Zocoro' can be compared to the cultivars 'Propertius' (not patented) and 'Markham's Pink' (not patented). Comparisons of the staminodes and tepals between 'Zocoro' and 'Markham's Pink' and 'Zocoro' and 'Propertius' are provided in TABLE 1.

TABLE 1

| 'Markham's Pink' | 'Zocoro' |
|---|---|
| Staminodes: | Staminodes: |
| Lanceolate<br>Pale purple<br>Outer usually not forming a perfect rosette | Linear<br>Pale purple to almost white at base<br>Outer usually forming a perfect rosette |
| Tepals: | Tepals: |
| Outside purple with darker base and paler margin | Outside rather equally coloured pale purple with just only slightly darker purple towards the base |
| **'Propertius'** | **'Zocoro'** |
| Staminodes: | Staminodes: |
| Usually irregularly bending and wavy, not equal in length | Usually rather straight and equal in length |
| Tepals: | Tepals: |
| Outside dark purple and clearly ribbed | Outside pale purple and not ribbed |

BRIEF DESCRIPTION OF THE DRAWING

The accompanying colored photographs illustrate the overall appearance and distinct characteristics of the new *Clematis*. The photographs were taken of a three year-old plant of 'Zocoro' as grown in a one-gallon container in Boskoop, The Netherlands.

The photograph in FIG. 1 shows the flowering habitus.

Figure 1:
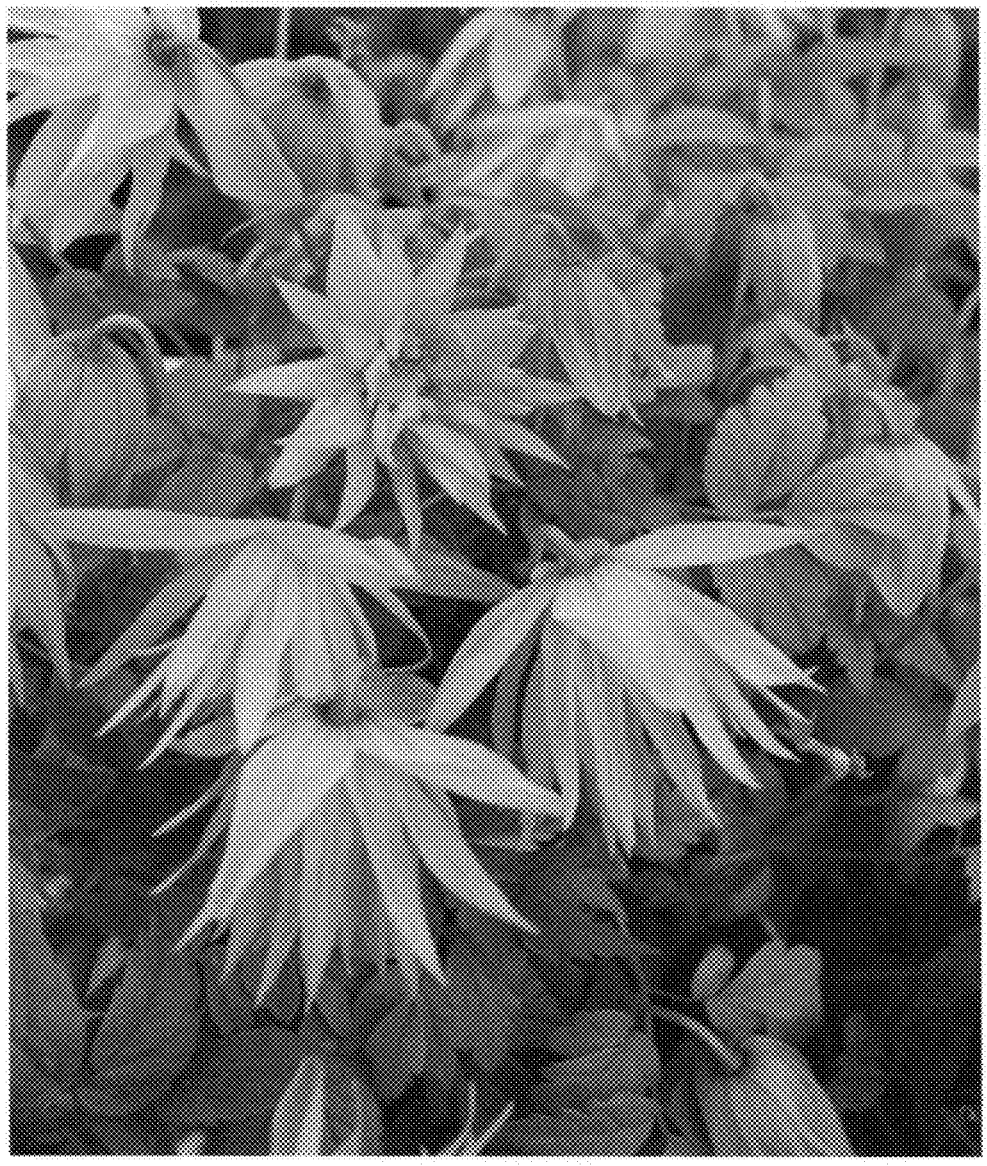
Figure 2:
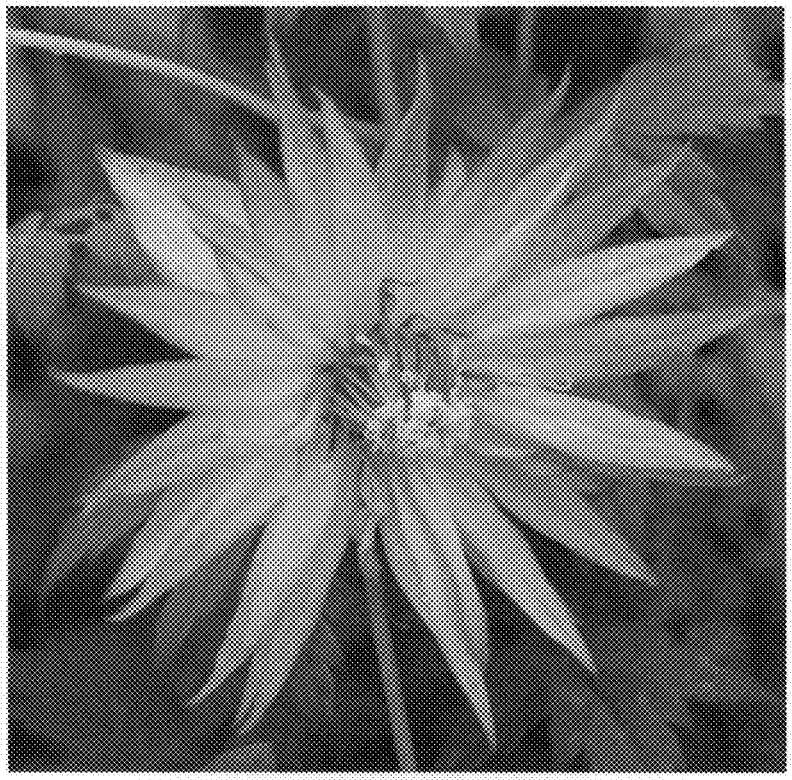
FIG. 2 shows the inside of the flower with tepal-like staminodes and pistils.
Figure 3:
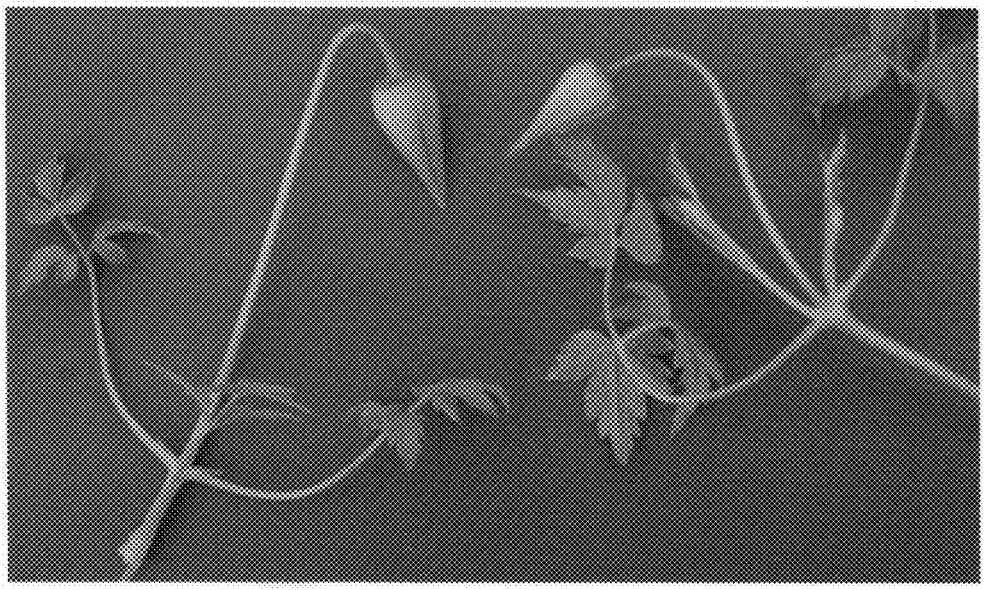
FIG. 3 shows the flower buds.
Figure 4:
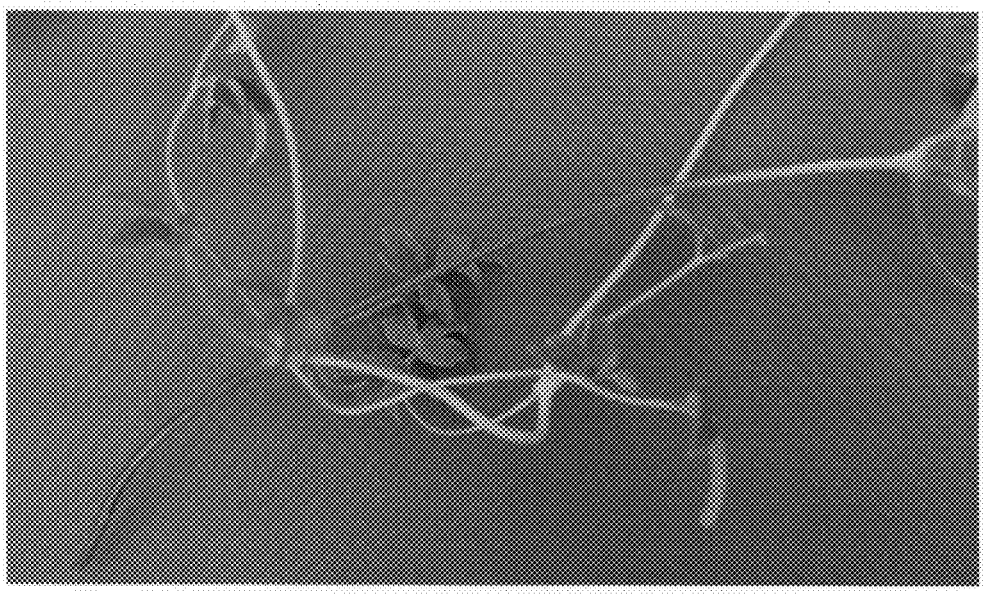
FIG. 4 shows old and new part of the stem with a node.
Figure 5:
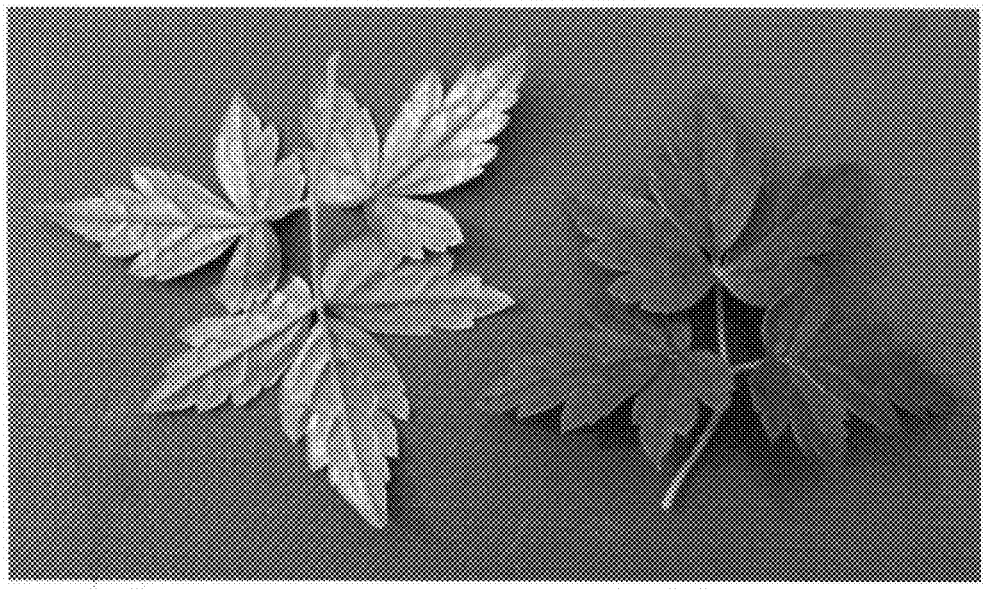
FIG. 5 shows 2 leaves with upper and lower surface.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of two year-old plants of *Clematis* 'Zocoro' as grown outdoors in full sun in one-gallon containers at a nursery in Boskoop, The Netherlands. The phenotype of the new cultivar may vary with variations in environmental, climatic and cultural conditions, as the cultivar has not been tested under all possible environmental conditions. The color determination is in accordance with The 2001 R.H.S. Colour Chart, London, England, except where general color terms of ordinary dictionary significance are used.

General description:

*Botanical classification.*—*Clematis* 'Zocoro' (classified in the Atragene Group).

*Blooming period.*—Spring with a few flowers in summer.

*Plant habit.*—Herbaceous climber.

*Height and spread.*—Three year-old plant is about 50 cm in width at the base and 2 m in height when slightly pruned after spring flowering.

*Cold hardiness.*—At least to U.S.D.A. Zone 5.

*Culture.*—Well-drained soils in full sun with the roots shaded.

*Diseases and pests.*—Susceptibility to phytophthora, especially in winter.

*Root description.*—Fibrous.

Growth and propagation:

*Propagation.*—Internodial soft wood cuttings from vegetative shoots.

*Root initiation.*—Roots develop in 6 weeks in summer under greenhouse conditions.

*Time required for root development.*—75 to 90 days to develop a 5-cm container from a cutting 5 cm in length.

*Growth rate.*—Moderately vigorous once planted in the landscape.

Stem description:

*Shape.*—Round and slightly 6-ribbed.

*Stem color.*—N144A on young shoots and 59A in color on older shoots at upper side.

*Stem size.*—About 2 m in length (including peduncle and terminal pedicel), an average of 2 to 4 mm in diameter.

*Stem surface.*—Glabrous with a few scattered hairs.

*Internode length.*—Ranges from 4 to 10 cm.

*Branching.*—Branching from the base and from below the flower.

Foliage description:

*Leaf arrangement.*—Opposite.

*Leaf division.*—Subbitemate.

*Leaf size.*—Up to 7 cm in length and 8 cm in width.

*Leaf attachment.*—Petiolate.

*Leaflet shape.*—Lanceolate.

*Leaflet base.*—Oblique or cordate.

*Leaflet apex.*—Acuminate.

*Leaflet fragrance.*—Fresh "green" fragrance when crushed.

*Leaflet venation.*—Upper surface with deep veins, lower surface with raised veins, both surfaces match leaf color.

*Leaflet margins.*—A few large teeth and usually 1 lobe.

*Leaflet attachment.*—Petiolulate.

*Leaflet surface.*—Upper surface glabrous but a few very short hairs at the main veins, lower surface sparsely hairy.

*Leaflet size.*—Up to 3.5 cm in length and 3.5 cm in width.

*Leaflet color.*—Upper surface 137A, lower surface 143B in color and glossy.

*Petioles and petiolules.*—Petiole up to 5 cm in length, 143C in color, round, surface with a few scattered hairs; petiolule up to 2 cm in length, 143C in color, round, surface with a few scattered hairs.

Inflorescence description:

*Inflorescence type.*—Solitary.

*Inflorescence arrangement.*—Terminal.

*Peduncles.*—Up to 10 cm in length, 144A in color but stained 59D near flower, round but slightly ribbed at base, surface sparsely hairy.

*Pedicels.*—No pedicel.

*Flower buds.*—Nodding, lanceolate in shape, apex acuminate, base obtuse, 144C in color flushed 59D.

*Flower fragrance.*—None.

*Lastingness of the flowers.*—Individual flowers last up to about 6 to 9 days but the tepals and tepal-like staminodes remain attached much longer.

*Flower quantity.*—Average of 10 to 15 per stem.

*Flower type.*—Campanulate.

*Flower aspect.*—Nodding.

*Flower size.*—Average of 4 to 7 cm in diameter.

*Flower sex.*—Unisexual.

*Tepal number.*—Average of 4.

*Tepal arrangement.*—Un-fused with very slight overlapping at base.

*Tepal shape.*—Lanceolate.

*Tepal apex.*—Acuminate.

*Tepal base.*—Obtuse.

*Tepal margin.*—Entire.

*Tepal surface.*—Inner surface glabrous but a few hairs, outer surface sparsely hairy with villous margin.

*Tepal color.*—Inner surface 62B in color with a small 144C base, outer surface 62A with veins 61B and 61A base 61A.

*Tepal size.*—Up to 4 cm in length and 1.3 cm in width.

Reproductive organs:

*Gynoecium.*—Numerous pistils (70 to 100), up to 1.4 cm in length, ovary glossy N144A in color, style silvery plumose, stigma 145D in color, bend and glabrous.

*Androcoecium*.—Usually no fertile stamens but in summer flowers a few, almost fertile-like staminodes with sterile sub-anthers, 0.6 to 1.1 cm in length, 0.1 cm in width, linear, 144D in color, hairy, 20 to 30 tepal-like staminodes, linear, up to 4 cm in length, 0.2 to 0.5 cm in width, apex acuminate, base cuneate, margin entire, 62B in color to N155C at the base, inner surface a few hairs, outer surface hairy.

*Seed*.—Seed are rarely formed and not available for data collection.

It is claimed:

1. A new and distinct cultivar of *Clematis* plant named 'Zocoro' as herein illustrated and described.

* * * * *

UNITED STATES PATENT AND TRADEMARK OFFICE

CERTIFICATE OF CORRECTION

PATENT NO. : PP24,642 P2
APPLICATION NO. : 13/507983
DATED : July 15, 2014
INVENTOR(S) : Jan van Zoest It is certified that error appears in the above-identified patent and that said Letters Patent is hereby corrected as shown below:

Title page, item [73] Assignee:

Delete:
J. Van Zoesl Behler B.V., Boskoop (NL)

Insert:
J. Van Zoest Beheer B.V., Boskoop (NL)

Signed and Sealed this
Thirtieth Day of September, 2014

Michelle K. Lee

Michelle K. Lee
*Deputy Director of the United States Patent and Trademark Office*